US006297015B1

(12) United States Patent
Shafran

(10) Patent No.: US 6,297,015 B1
(45) Date of Patent: Oct. 2, 2001

(54) CROHN'S DISEASE DIAGNOSTIC AND TREATMENT METHODS AND COMPOSITIONS

(76) Inventor: Ira Shafran, 1316 Greencove Rd., Winter Park, FL (US) 32789

( * ) Notice: Subject to any disclaimer, the term of this patent is extended or adjusted under 35 U.S.C. 154(b) by 0 days.

(21) Appl. No.: 09/404,095

(22) Filed: Sep. 23, 1999

Related U.S. Application Data

(60) Provisional application No. 60/101,579, filed on Sep. 24, 1998.

(51) Int. Cl.$^7$ ................... G01N 33/569; C12N 15/31; C12Q 1/68; C12P 19/34
(52) U.S. Cl. ............... 435/6; 435/4; 435/5; 435/7; 435/7.21; 435/91.2; 435/320.1; 435/29; 435/34; 435/91; 435/863; 435/7.32; 435/7.24; 435/2; 435/811; 436/94; 436/501; 436/518; 436/811; 436/507; 436/544; 436/546; 436/863; 514/17; 514/18; 935/77; 935/78; 536/22.1; 536/28; 536/27; 536/26; 536/29
(58) Field of Search ................ 435/4, 5, 6, 7, 435/7.21, 91.2, 320.1, 29, 34, 91, 863, 7.32, 7.24, 2, 811; 436/94, 501, 518, 811, 507, 544, 546, 863, 8, 9, 11, 15, 16; 514/17.18; 536/22.1, 28, 27, 26, 29; 935/77, 78

(56) References Cited

U.S. PATENT DOCUMENTS

| | | | |
|---|---|---|---|
| 4,918,178 | * | 4/1990 | Hurley et al. ............... 536/27 |
| 5,225,324 | * | 7/1993 | McFadden et al. ........... 435/6 |
| 5,334,504 | * | 8/1994 | Wood et al. ............... 435/7.32 |
| 5,776,692 | | 7/1998 | El-Zaatari et al. . |
| 5,795,858 | * | 8/1998 | Michaelis et al. ........... 514/8 |

FOREIGN PATENT DOCUMENTS

WO 92/16628  * 10/1992  (GB)  ............... C12N/15/31

OTHER PUBLICATIONS

Gui, Thomas, Tizard, Lake, Sanderson, and Taylor, Two–Year Outcomes Analysis of Crohn's Disease Treated with Rifabutin and Macrolide Antibiotics, *Journal of Antimicrobial Chemotherapy*, 1997.

NACC, Does *Mycobacterium paratuberculosis* cause Crohns disease?, Mar. 15, 1997.

Gutknecht, Dire Warning About Johne's Disease, *DairyBiz—Animal Health*, Jan., 1998.

Susman, The Hunt for an Elusive Bacterium: Can Killing *M. paratuberculosis* Put Crohn's in Remission?, *Gastroenterology & Endoscopy News*, Sep., 1996.

El–Zaatari, Graham, and Naser, 35K Encoding Gene and its Product from *Mycobacterium paratuberculosis*, *BCM Technologies, Inc.*, 1996.

Shafran, Piromalli, and Naser, Endoscopic Healing of Crohn's After Antibiotic Treatment, Abstract presented at *99th Annual Meeting of the American Gastroenterology Association*, published in Gastroenterology, vol. 116, Num. 4, Apr. 1999.

Shafran, Fenster, Piromalli, Romero, Schwartz, Campbell, El–Zataari and Naser, Humoral Immune Response of Crohn's Patients for Mycobacterium avium subspecies paratuberculosis, Abstract presented at *99th Annual Meeting of the American Gastroenterology Association*, published in Gastroenterology, vol. 116, Num. 4, Apr. 1999.

Shafran, Fenster, Piromalli, Romero, Schwartz, Campbell, and Naser, In Vitro Evaluation of Anti–Tuberculosis Drugs Against *Mycobacterium avium ss. paratuberculosis* For Treatment of Crohn's Disease, Abstract presented at *99th Annual Meeting of the American Gastroenterology Association*, published in Gastroenterology, vol. 116, Num. 4, Apr. 1999.

Shafran, Fenster, Piromalli, Romero, Schwartz, Campbell, and Naser, Rapid Culturing and PCR Detection of *Mycobacterium avium ss paratuberculosis* from Crohn's Disease Tissue, Abstract presented at *99th Annual Meeting of the American Gastroenterology Association*, published in Gastroenterology, vol. 116, Num. 4, Apr. 1999.

* cited by examiner

*Primary Examiner*—Long V. Le
*Assistant Examiner*—Lisa V Cook
(74) *Attorney, Agent, or Firm*—Allen, Dyer, Doppelt, Milbrath & Gilchrist, P.A.

(57) ABSTRACT

A composition and method for detecting Crohn's disease include the use of serological testing as a rapid and simple way to diagnose Crohn's disease. The serological tests were based on the use of the two recombinant clones isolated from an *M. paratuberculosis* genomic library that expressed 35K and 36K MW antigens. Antigen p35 was isolated from Johne's disease sera (acid-fast bacilli form) and p36, from human CD sera (spheroplast form). The combined use of p35 and p36 recombinant antigens provides a highly specific and sensitive test to demonstrate the humoral immune response of CD patients to *M. paratuberculosis*. A serologic kit is disclosed including the composition including the combined p35 and p36 antigens. A treatment methodology utilizes antimycobacterial drugs, preferably upon patients prescreened for the presence of *M para*. A particular antibiotic regimen includes an administration of both rifabutin and clarithromycin, which has been found to be particularly effective in alleviating the symptoms of Crohn's disease.

3 Claims, No Drawings

CROHN'S DISEASE DIAGNOSTIC AND TREATMENT METHODS AND COMPOSITIONS

CROSS-REFERENCE TO RELATED APPLICATION

This application claims priority from provisional application "Crohn's Disease Diagnostic Method and Composition," Ser. No. 60/101,579, filed Sep. 24, 1998.

BACKGROUND OF THE INVENTION

1. Field of the Invention

The present invention relates to compositions and methods for diagnosing and treating Crohn's disease, and, more particularly, to such compositions and methods for screening for a presence of a bacterium believed involved in causing Crohn's disease and for treating patients shown by the screening method to be infected with the bacterium.

2. Description of Related Art

Crohn's disease is an inflammatory bowel disease that affects 2–3 million Americans, with a typical onset between 15 and 25 years of age. Crohn's is a chronic disorder that causes inflammation or ulceration in the small and/or large intestine, extending into the deeper layers of the intestinal wall. Sometimes the inflammation may also affect the mouth, esophagus, stomach, duodenum, appendix, or anus. Although Crohn's is a chronic condition, periods of remission may occur, with recurrences unpredictable. Two forms of the disease, perforating and nonperforating, are believed to occur.

Common symptoms of Crohn's disease include abdominal pain and diarrhea. There may also be rectal bleeding, weight loss, and fever. The bleeding may be serious and persistent, leading to anemia. Children may suffer delayed development and stunted growth.

Current diagnoses are performed by blood test to detect anemia and elevated white blood cell count, colon biopsy, and lower gastrointestinal x-ray series.

There are drugs that can be helpful in controlling Crohn's disease, but at present there is no cure. Treatment is aimed at correcting nutritional deficiencies, controlling inflammation, relieving the symptoms of abdominal pain, diarrhea, and rectal bleeding. Drugs known to be used for this condition can help, but side effects can be deleterious. Surgeries that may be performed to alleviate symptoms include the removal of inflamed areas, draining of abscesses, and bowel resection.

The cause of Crohn's disease has been debated since its recognition in the early part of the twentieth century. There are those who believe that at least some of the cases are caused by a bacterium, specifically Mycobacterium paratuberculosis, which is endemic in foods derived from cattle and water supplies in the Western world. Crohn's patients have been reported to have been cured by an antibiotic or a multidrug antibiotic regime having activity against that organism.

Mycobacterium paratuberculosis is an obligate pathogen; that is, it cannot multiply outside the cells of animals. It is known to be present in a wide variety of animals, including primates and humans. The best-studied animal paratuberculosis is bovine Johne's disease (BJD), a disease that causes chronic diarrhea, weight loss, and malnutrition in cattle and affects up to 25% of the dairy cattle in the United States. Cows infected with BJD are known to secrete Mycobacterium paratuberculosis in their milk, which is not destroyed by standard milk pasteurization methods, but only by ultra-pasteurization. This bacterium has also been cultured from a municipal water supply in the United States.

One can be exposed to Mycobacterium paratuberculosis and not develop Crohn's disease, if the immune system is capable of fighting the bacterium, resulting only in a transient intestinal infection with no after-effects. However, those susceptible to inflammatory bowel disease, including those with a genetic predisposition or being immunosuppressed, can develop the disease.

Mycobacterium paratuberculosis occurs in two forms, the bacillary form and the spheroplast form, in which no cell wall is present. The former, which may be required to cause disease, is easily detected in animals by a simple chemical test; the latter, however, has only been found to be detectable with genetic testing techniques, such as polymerase chain reaction (PCR), to detect the 1451-bp IS900 insertion sequence unique to Mycobacterium paratuberculosis. PCR methods, however, can fail under conditions in which the amount of spheroplast present in the tissue is low or when tissue preserved in wax-embedded paraffin blocks is used. Another method is direct culturing of the organism followed by IS900 detection.

Currently available serological tests for Johne's disease are believed to have poor sensitivity and specificity, and fecal smear microscopy and fecal culture in early stages of infection are of limited value. El-Zaatari et al. (Current Microbiol. 29, 177–184, 1994) have reported using the chromosomal DNA of a Mycobacterium paratuberculosis strain to construct an expression genomic library in E. coli. A recombinant clone, p35, that expresses a protein of approximately 35K was identified, and its gene product was used in the serodiagnosis of Johne's disease by immunoblotting. El-Zaatari et al. reported a diagnostic yield with this clone that was higher than those reported using commercially available diagnostic tests. They suggest that the high sensitivity and specificity of p35 indicates a potential utility for the diagnosis of animals at all stages of Johne's disease.

El-Zaatari et al. also tested the clone's potential as a probe, and found that it hybridized specifically to nine bacterial strains representing the Mycobacterium avium complex species and none of the other mycobacterial species or other related and unrelated bacteria.

Recently El-Zaatari et al. (U.S. Pat. No. 5,776,692) have reported a recombinant clone pMptb #48 that expresses a 36K M. paratuberculosis antigen and its use as a test, as well as a mycobacterial genus-specific DNA probe corresponding to a 1.4 kb BamH 1-DNA insert in pMptb #48. Serological tests are suggested for using the clone and/or the p36k protein or fragments thereof

SUMMARY OF THE INVENTION

It is therefore an object of the present invention to provide a composition and method for screening for an infection caused by Mycobacteriurm avium, such as Crohn's disease.

It is an additional object to provide such a composition and method that have improved specificity and sensitivity over prior known compositions and methods.

It is a further object to provide such a composition and method that do not require a surgical procedure to obtain a test sample.

It is another object to provide such a composition and method that are serological in nature.

An additional object is to provide a composition and method for predicting a predisposition to Crohn's disease.

A further object is to provide a composition and method for treating patients shown by the screening method to be infected with Mycobacterium paratuberculosis.

These objects and others are attained by the present invention, a composition and associated methods for detecting and treating a M. para. infection such as Crohn's disease in a human and for predicting a genetic predisposition thereto.

The detecting composition in a first embodiment comprises a combination of the p35 and p36 clones.

In a second embodiment the detecting composition comprises a combination of the 35K and 36K proteins expressed by the p35 and p36 clones, respectively.

In a first embodiment of the detection method of the present invention, a combination of the 35K and 36K proteins is used as an antigen and reacted with serum samples to detect for the presence of a M. para. infection, and thus for the presence of Crohn's disease, at least some cases of which are believed to be caused by M. paratuberculosis.

An embodiment of the treatment composition of the present invention comprises at least one antibiotic effective in the eradication of M. paratuberculosis.

In an embodiment of the treatment method, the effective antibiotic is administered to a patient having been found positive for M. paratuberculosis by the serologic method of the invention.

The features that characterize the invention, both as to organization and method of operation, together with further objects and advantages thereof, will be better understood from the following description.

DETAILED DESCRIPTION OF THE PREFERRED EMBODIMENTS description of the preferred embodiments of the present invention will now be presented.

The p35 and p36 recombinant clones were used to perform humoral response testing to confirm M. paratuberculosis infection by detecting the presence of specific antibodies in a patient. Although a positive response does not by itself indicate active infection, the quantitative measure of antibody titre supported by cutoff values may indicate infection activity levels. Serological testing requires only blood samples from subjects rather than the endoscopic or surgical procedures required to obtain tissue. Because false negatives can occur in BCG- and PPD-positive patients, patient history screening is necessary. Serological testing is thus believed to be a rapid and simple way to diagnose Crohn's disease.

The serological tests were based on the use of the two recombinant clones isolated from an M. paratuberculosis genomic library that expressed 35K and 36K MW antigens. Antigen p35 was isolated from Johne's disease sera (acid-fast bacilli form) and p36, from human CD sera (spheroplast form). The combined use of p35 and p36 recombinant antigens provides a highly specific and sensitive test to demonstrate the humoral immune response of CD patients to M. paratuberculosis.

Data were collected on 110 human sera, of which 63 were Crohn's patients and 47 controls (see Table 1). Among the controls were 35 volunteers with no history of GI tract disorder and 12 with ulcerative colitis. Subjects were free of tuberculosis and leprosy and had not received a bacillus calmet guerin (BCG) vaccination. The analysis was conducted using immunoblot against rabbit hyperimmune anti-M. para. antibodies. Of the 63 Crohn's sera tested, 49 (78%) reacted with p35, 57 (90%) with p36, 48 (76%) with both antigens, and 58 (92%) with either antigen. A small portion of Crohn's samples, 5 (8%), did not react with one or both. Of the 35 sera from normal controls, none (0%) reacted with both antigens, 4 (11%) with p36, 5 (14%) with p35, and 9 (25%) with either antigen. Of the 12 ulcerative colitis sera, only 1 (10%) reacted with p35 and/or p36, individually or combined.

TABLE 1

Serological Results

| | # tested | +ve for p35 | +ve for p36 | +ve for either p35 or p36 | +ve for both p35 and p36 |
|---|---|---|---|---|---|
| Crohn's disease | 63 | 45 (78%) | 57 (90%) | 58 (92%) | 48 (76%) |
| Ulcerative colitis | 12 | 1 (8%) | 1 (8%) | 1 (8%) | 1 (8%) |
| Normal controls | 35 | 5 (14%) | 4 (11%) | 9 (35%) | 0 (0%) |

These data suggest that using a combination of p35 and p36 antigens rather than individually is more specific for Crohn's disease diagnosis in an unexpectedly synergistic manner. Using both antigens does reduce the sensitivity of the assay but significantly increases the specificity. The data also confirm that there is a difference in reactivity between Crohn's samples and the controls at a reasonable level of significance ($P < 0.001$) and further strengthens the association between Crohn's disease and M. paratuberculosis.

The data also support an improved serologic kit comprising the composition of the invention to provide earlier diagnosis and better treatment of Crohn's disease.

With the indication that Crohn's disease is at least in part caused by the presence of M. paratuberculosis, a treatment regimen including an administration of antituberculosis drugs was proposed. However, this bacterium is known to be resistant to most of these drugs. An in vitro study was performed to evaluate seven anti-TB drugs against M. para. isolated from resected tissue of CD patients using the Bactec system, which is known in the art, and the results are given in Table 2.

TABLE 2

Results of in vitro test of Seven Antituberculosis Drugs against *M. para.*

|  | RIF[a] | ST[b] | KM[c] | CLR[d] | INH[e] | PZA[f] | EMB[g] | RIF:EMB | RIF:CLR |
|---|---|---|---|---|---|---|---|---|---|
| MIC$_{50}$ (μg/ml)[h] | >1.0 | >0.4 | <1.3 | <0.25 | >20 | >20 | <0.5 | <1.0:0.2 | <0.5:0.3 |
| MIC$_{99.9}$ (μg/ml)[i] | >2.6 | >3.0 | <3.0 | <1.25 | >20 | >20 | <3.0 | <1.0:1.0 | <0.5:1.2 or 1.0:0.76 |
| Status[j] | R | R | R | S | R | R | S | S | S |

[a]Rifampicin; [b]streptomycin; [c]kanamycin; [d]clarithromycin; [e]isoniazid; [f]pyrazinamide; [g]ethambutol; [h,i]50, 99.9% *M. para.* cells inhibited or killed, resp.; [j]R, resistant; S, sensitive.

Twenty-nine CD patients who tested serologically positive for *M. para.* were selected for rifabutin and macrolide antibiotic therapy (RMAT) for a duration of 6 months to 1 year based upon their overall response to the treatment. The regimen included 250 mgm po bid clarithromycin, 150 mgm 1 po bid rifabutin, and 200 mgm po qd of a probiotic containing equal amounts of *Lactobacillus acidophilus* and *Lactobacillus rhamnosus*.

After 3 months all the patients were assessed to determine overall response to the treatment. 28% (8/29) of the patients achieved a state of clinical remission (as defined by the CDAI criteria with a score <150) while being off all other medications. The majority of these patients had acute presentation of CD when placed on RMAT. 31% (9/29) of the patients were not in clinical remission but experienced significant improvements as they discontinued the use of all other Crohn's medications. 28% (8/29) of the patients noticed some improvements on RMAT but were still using traditional medications, such as sulfasalazine and corticosteroids. 14% (4/29) were nonresponders, since they were unable to tolerate the RMAT medications and discontinued therapy. These findings support the use of RMAT in the treatment of CD.

In a particular case study, a 65-year-old patient having been diagnosed with Crohn's disease at age 30 was found to be PCR positive for *M. para.* with humoral immune response against recombinant antigens of *M para.* An endoscopy was performed through the patient's stoma and found a 4.0-cm aphthous ulcer. The remaining ileum was unremarkable to a depth of 120 cm. Histology indicated typical features of CD.

The patient demonstrated significant healing (80%) of an ulcer seen in the ileum by endoscopy following a regimen of 250 mg clarithromycin twice a day and 150 mg rifabutin daily. The patient became asymptomatic in 2 weeks, and a followup endoscopy was performed after completing 1 month of treatment. The 4-cm ulcer had reduced in size to 1 cm, with excellent reepitheliazation from the edge of the ulcer inward. The remaining ileum to 120 cm was normal. The patient has remained symptom-free and continues on the antibiotic regimen.

As this study was continued, 35 patients with CD were being treated with RMAT. 37% (13/35) of the patients developed a serum sickness-like illness during the first 4–6 weeks of treatment. The patients experienced flu-like symptoms such as fever, chills, moderate to severe arthralgia, back pain, anorexia, and fatigue. These symptoms generally lasted for a full week and dissipated over the following 3 weeks. With each patient, a majority of symptoms stopped within the first month of treatment. It was also found that these symptoms responded well to Cox-2 inhibitors (celecoxib—200 mgm po qd) with no adverse effects or worsening of colitis noted during treatment. These observations suggest that the Cox-2 inhibitors may help in controlling the initial side effects of RMAT. It is also thought that this serum sickness may be a Jarisch-Herxheimer reaction in response to the antimicrobial therapy.

Current hypotheses are being investigated regarding the causative agent(s) of Crohn's disease. While many workers in the field have become convinced of the involvement of *M. para.*, it may well turn out that this bacterium is but one of a number of pathogenic agents. Therefore, the regimen proposed herein preselects patients for antibiotic treatment by the detecting method of the present invention, the combined p35/p36 serological test, patients testing negative for *M. para.* being less likely to experience alleviation of CD symptoms under the antibiotic regimen.

It may be appreciated by one skilled in the art that additional embodiments may be contemplated, including other recombinant clones chosen from the *M. paratuberculosis* genomic library and other antibiotic regimens for the treatment of bacteria-positive CD patients.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the compositions and methods illustrated and described herein are by way of example, and the scope of the invention is not limited to the exact details of structure, synthesis, and delivery.

What is claimed is:

1. An improved method for screening for Crohn's disease in a human comprising the steps of:
    simultaneously contacting a human serum sample with an antigen composition comprising:
        a 35 kD protein expressed by a recombinant p35 clone specific to sera from Johne's disease; and
        a 36 kD protein expressed by a recombinant p36 clone specific to sera from Crohn's disease;
        detecting a bound antibody-antigen complex to said antigen composition, wherein said bound antibody-antigen complex detects the presence of *Mycobacterium paratuberculosis*, and thus indicates the presence of Crohn's disease.

2. The method recited in claim 1, wherein the detecting step comprises conducting an immunoblot test against rabbit hyperimmune anti-*Mycobacterium paratuberculosis* antibody.

3. A method for screening for the presence of an infection caused by *Mycobacterium paratuberculosis* comprising the steps of:

simultaneousely contanting a human serum sample with an antigen composition comprising:

a 35 kD protein expressed by a recombinant p35 clone specific to sera from Johne's disease; and a 36 kD protein expressed by a recombinant p36 clone specific to sera from Crohn's disease;

detecting a bound anti-antibody complex to said antigen composition, wherein said bound antibody-antigen complex indicates a presence of an infection caused by *Mycobacterium paratuberculosis*.

* * * * *